United States Patent [19]

Inamoto et al.

[11] Patent Number: 5,352,349

[45] Date of Patent: Oct. 4, 1994

[54] METHOD FOR REVIVING AN ELECTRODE OF A BIOSENSOR

[75] Inventors: Tomoyuki Inamoto, Kusatsu; Hidetaka Fujimura, Kusatsu; Yasuhiro Nagata, deceased, late of Kusatsu, all of Japan, Yuko Nagata, Yasutaka Nagata, heir

[73] Assignee: Daikin Industries, Ltd., Japan

[21] Appl. No.: 1,197

[22] Filed: Jan. 7, 1993

Related U.S. Application Data

[63] Continuation-in-part of Ser. No. 574,788, Aug. 30, 1990, abandoned, and a continuation-in-part of Ser. No. 574,790, Aug. 30, 1990, abandoned.

[30] Foreign Application Priority Data

Aug. 30, 1989 [JP] Japan .................................. 1-223613
Aug. 30, 1989 [JP] Japan .................................. 1-223614

[51] Int. Cl.$^5$ ........................................ G01N 27/327
[52] U.S. Cl. ................. 204/153.12; 204/402; 204/403; 204/415
[58] Field of Search ............. 204/153.12, 153.17, 204/402, 403, 415

[56] References Cited

U.S. PATENT DOCUMENTS

| | | | |
|---|---|---|---|
| 4,166,775 | 9/1979 | Bruckenstein et al. | 204/415 |
| 4,477,314 | 10/1984 | Richter et al. | 204/402 |
| 4,566,949 | 1/1986 | Berger | 204/402 |
| 4,772,375 | 9/1988 | Wullschleger et al. | 204/402 |
| 4,804,454 | 2/1989 | Asakura et al. | 204/425 |
| 4,897,162 | 1/1990 | Lewandowski et al. | 204/402 |
| 4,950,378 | 8/1990 | Nagata | 204/402 |
| 5,288,387 | 2/1994 | Ito et al. | 204/402 |

FOREIGN PATENT DOCUMENTS

| | | |
|---|---|---|
| 48443/85 | 5/1986 | Australia . |
| 0103109 | 3/1984 | European Pat. Off. . |
| 3822911 | 1/1989 | Fed. Rep. of Germany . |
| 0060255 | 4/1982 | Japan .................... 204/402 |
| 1531761 | 11/1978 | United Kingdom ........ 204/402 |
| 2019580 | 10/1979 | United Kingdom . |
| 2201248 | 11/1988 | United Kingdom . |

OTHER PUBLICATIONS

Patent Abstracts of Japan, vol. 7, No. 125 (P-200) (1270) May 31, 1983, JP-A-58 041344 (Baionikusu Kiki K. K.) Mar. 10, 1983.

Patent Abstracts of Japan, vol. 9, No. 329 (P-416) (2052) Dec. 24, 1985, JP-A-60 155969 (Matsushita Denko K. K.) Aug. 16, 1985.

*Primary Examiner*—T. Tung
*Attorney, Agent, or Firm*—Beveridge, DeGrandi Weilacher & Young

[57] ABSTRACT

After a reverse bias is applied between a working electrode and a counter electrode or a reference electrode, a forward bias higher than a forward measurement bias is applied between the working electrode and the counter electrode or the reference electrode, before the forward measurement bias is applied. This reduces the time period before which an actual measuring operation is possible. When the bias is applied between the working electrode and the counter electrode or reference electrode, the bias is gradually increased in absolute value according to a predetermined time constant. This reduces damage to the membrane or membranes fixed on a surface of the electrode unit.

8 Claims, 7 Drawing Sheets

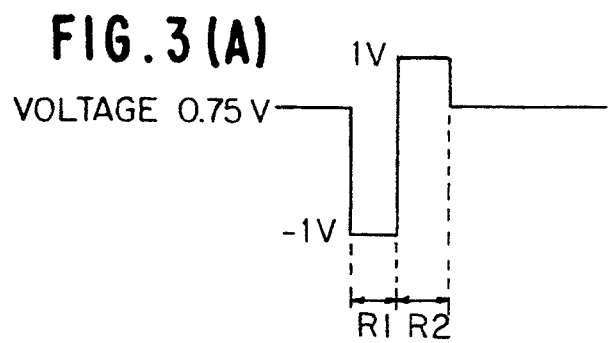
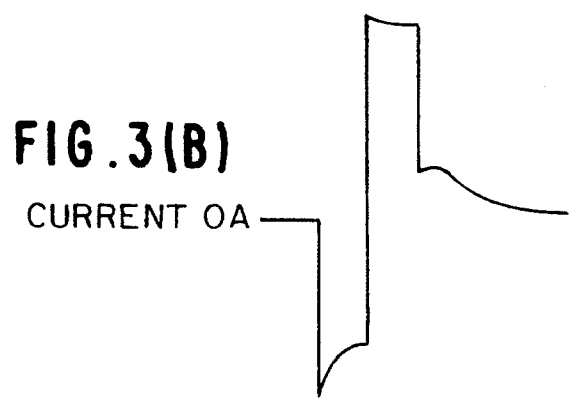
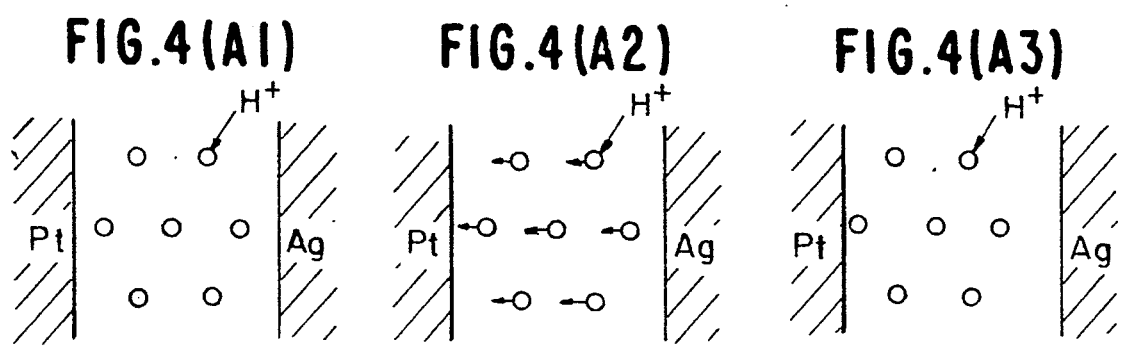
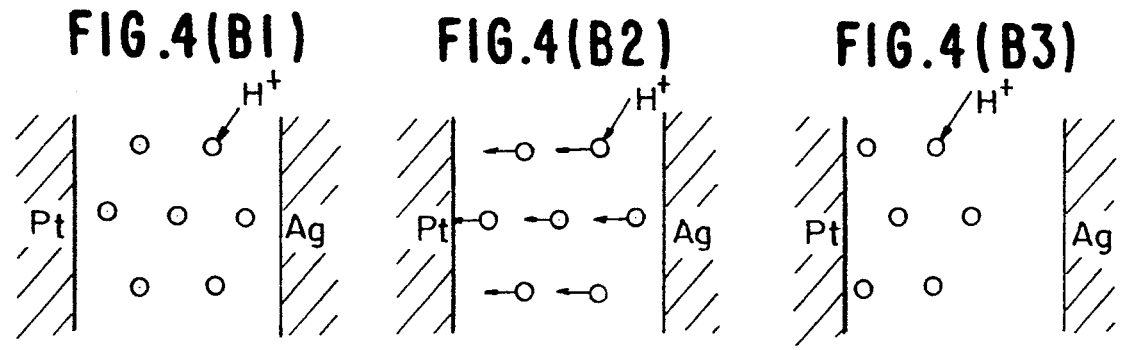

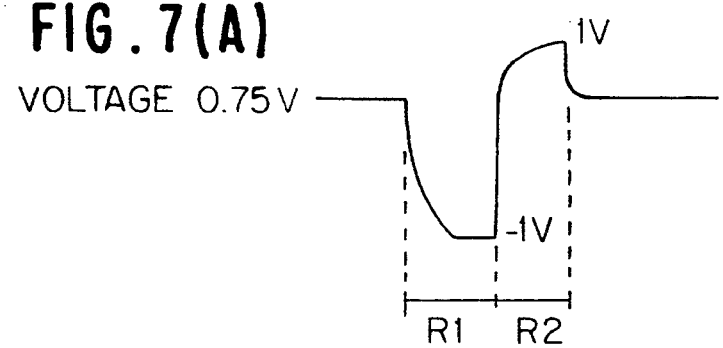
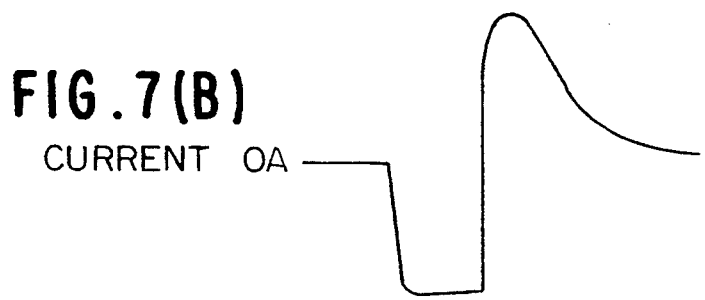
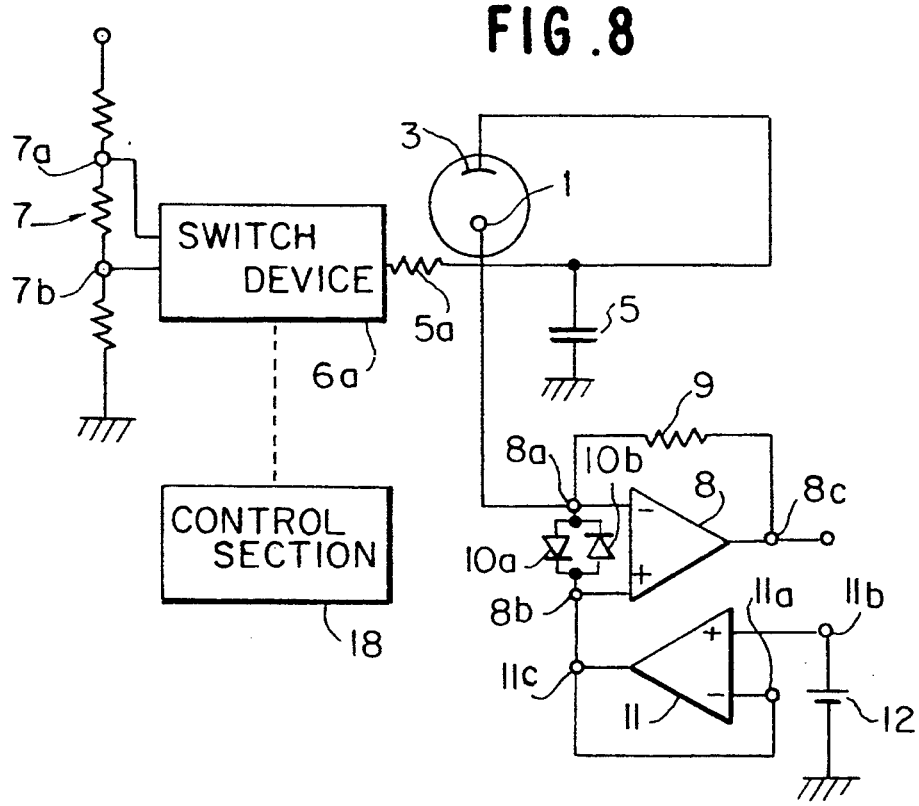

METHOD FOR REVIVING AN ELECTRODE OF A BIOSENSOR

This application is a continuation-in-part of U.S. application Ser. No. 07/574,788, now abandoned and U.S. application Ser. No. 07/574,790, both filed on Aug. 30, 1990, now abandoned.

BACKGROUND OF THE INVENTION

The present invention relates to methods and apparatus for reviving an electrode of a biosensor, and more particularly to methods and apparatus for reviving an electrode of a biosensor by supplying a bias having a different polarity from the measurement bias polarity to the electrode before a measuring operation is started.

It is known that a physiologically active substance is capable of selectively detecting a very complicated organic compound, protein or the like with high sensitivity. With attention directed to this characteristic, research has been made in various biosensors.

A typical biosensor having an electrode unit and a physiologically active substance fixed thereon is proposed. The biosensor is used for detecting the existence of an object substance, the relative or active quantity of the object substance and the like based on an electrical signal output from the electrode unit corresponding to the biological reaction of the object substance, under the condition that a predetermined forward bias is applied to the electrode unit. For example, the electrode unit has a working electrode made of platinum and a counter electrode made of silver. An enzyme-immobilized membrane is fixed onto the electrode unit. When the object substance is to be measured, hydrogen peroxide is generated through an enzyme reaction of the object substance. Then, the generated hydrogen peroxide reaches the surface of the electrode unit through a hydrogen peroxide penetration membrane. The electrode unit outputs an electrical signal corresponding to the quantity of the hydrogen peroxide that reaches it. The existence of the object substance, the relative or active quantity of the object substance and the like are detected based on the electrical signal. Concretely, the working electrode has a forward bias of 0.6 volts applied with respect to the counter electrode.

In the biosensor described above, an interfering layer such as an oxidized layer and the like which interferes with electrical signals is generated on the working electrode, and the activity of the working electrode is lowered as the object substance measuring operation is continued with the forward bias being applied to the electrode unit. It is proposed that a reverse bias is accordingly applied to the electrode unit (the working electrode has a reverse bias of about −0.6 volts applied with respect to the counter electrode, corresponding to the concrete example) after one or more measurements are performed, within the time period in which the measurement is not performed, so as to remove the interfering layer. Then the activity of the working electrode is revived. The level of the output signal from the electrode unit is raised to the original level. (Refer to Japanese Patent Laid Open Sho 60-155959).

Lowered measuring sensitivity is recovered by applying the predetermined reverse bias voltage to the electrode unit during the time period in which the measurement is not performed, as is described above, then measuring with high sensitivity can be performed again.

In the reviving apparatus described above, a constant-voltage for reviving (reverse bias) is applied between the working electrode and the counter electrode. The oxidized layer on the working electrode is reduced, hydrogen, hydrogen ions and the like are accordingly generated. When a constant-voltage for measurement (forward bias) is applied between the working electrode and the counter electrode, a diffusion current flows depending upon the generated hydrogen, hydrogen ions and the like.

As a result, the electrical signal provided for measuring is affected by being lowered, by the diffusion current, so as to remarkably lower measuring accuracy just after the constant-voltage for measurement is applied between the working electrode and the counter electrode. When the measurement is performed after the diffusion current is sufficiently lowered, sufficient measuring accuracy is obtained, but a remarkably long waiting time period (for example, 1-2 minutes) is needed.

The same disadvantage as above arises for a biosensor having a reference electrode in addition to the working electrode and the counter electrode.

Also, in the reviving apparatus described above, reverse bias for reviving is applied between the working electrode and the counter electrode (refer to FIG. 13(A)) every predetermined time (for example, every hour) and just before starting of measurement. When the reverse bias for reviving is applied between the working electrode and the counter electrode, a large current flows in thin membranes fixed on a surface of an electrode unit (refer to FIG. 13(B)). Thin membranes, especially a selective penetration membrane being positioned close to the electrode unit, are gradually destroyed, thereby the penetration quantity of substances generated by the reaction or substances consumed by the reaction increases. For example, when the biosensor is used to measure glucose concentration, the hydrogen peroxide selective penetration membrane, made of a cellulose acetate membrane is destroyed, thereby the quantity of penetrating hydrogen peroxide increases. As a result, there is a disadvantage that an electrical signal provided from the electrode unit increases depending on the number of times a reviving operation occurs. Another disadvantage is that the life of the membrane or membranes is shortened by up to about one month. The life is a time period until a penetration ratio of the hydrogen peroxide selective penetration membrane increases by 10%.

SUMMARY OF THE INVENTION

It is an object of the present invention to shorten the time period between performing a reviving operation for an electrode unit to when it is possible to start a measuring operation for an object substance.

This present invention first applies a predetermined reverse bias to a working electrode for a predetermined time period, then applies forward bias higher than a forward measurement bias to the working electrode for a predetermined time period, then applies the forward measurement bias to the working electrode.

In this reviving method, an interfering layer on the working electrode which interferes with the turning on of electricity is reduced and the activity of the working electrode is revived by applying the reverse bias to the working electrode. Substances generated through reduction of the interfering layer are moved to one of the electrodes at high speed by applying the forward bias higher than the forward measurement bias to the working electrode. The substances are rapidly consumed, accordingly, when the forward bias is applied to the working electrode. As a result, a time period between performing a reviving operation for an electrode unit to when it is possible to start a measuring operation for an object substance with a predetermined accuracy maintained, is remarkably shortened.

The time period for applying the higher bias to the working electrode may be nearly equal to the time period for applying the reverse bias to the working electrode.

It is preferred that the predetermined reverse bias is a reverse bias which is gradually increased until its absolute value reaches a predetermined value. Damage of a membrane fixed on the surface of the electrode unit, effected by current is remarkably reduced.

It is also preferred that the higher forward bias is a forward bias which is gradually increased until its absolute value reaches a higher predetermined value than the forward bias for measuring. Damage of the membrane fixed on the surface of the electrode unit, effected by current is remarkably reduced.

It is further preferred that the predetermined reverse bias is a reverse bias which is gradually increased until its absolute value reaches a predetermined value, and the higher forward bias is a forward bias which is gradually increased until its absolute value reaches a predetermined value higher than the forward measurement bias. Damage of the membrane fixed on the surface of the electrode unit, effected by current is remarkably reduced.

This present invention comprises:
reviving voltage applying means for applying voltage for reviving to a working electrode;
measurement voltage applying means for applying voltage for measuring to the working electrode;
higher voltage applying means for applying a higher voltage than the voltage for measuring to the working electrode;
selection means for sequentially selecting a condition under which to apply a voltage for reviving to the working electrode from the reviving voltage applying means, a condition under which to apply a higher voltage to the working electrode from the higher voltage applying means, and a condition under which to apply a voltage for measuring to the working electrode from the measurement voltage applying means, when a measuring operation is to be performed.

In this reviving apparatus, the condition of applying voltage for reviving to the working electrode by the reviving voltage applying means and the condition of applying the higher voltage to the working electrode by the higher voltage applying means are selected in this order by the selection means, before an actual measuring operation is started. First, the interfering layer on the surface of the working electrode is removed. After the interfering layer has been removed, substances generated through removal of the interfering layer are moved to one of the electrodes at high speed by applying the higher forward bias to the working electrode. The substances are rapidly consumed when the forward bias is applied to the working electrode. As a result, after a short time period from when a reviving operation for an electrode unit has passed, a measuring operation for an object substance can be started with a predetermined accuracy maintained.

It is preferred that the reviving apparatus further comprises a first time constant means for applying a predetermined time constant to the reviving voltage. Damage of the membrane fixed on a surface of an electrode unit, effected by current is remarkably reduced.

It is also preferred that the reviving apparatus further comprises a second time constant means for applying a predetermined time constant to the higher voltage. Damage of a membrane fixed on a surface of an electrode unit, effected by current is remarkably reduced.

It is further preferred that the reviving apparatus further comprises a first time constant means for applying a predetermined time constant to the reviving voltage, and a second time constant means for applying a predetermined time constant to the higher voltage. Damage of a membrane fixed on a surface of an electrode unit, effected by current is remarkably reduced.

More specifically, the interfering layer easily can be removed by a reduction operation because the reviving operation is an operation to remove the interfering layer formed on the working electrode, and the interfering layer is generated by oxidization. When the interfering layer is removed, hydrogen, hydrogen ions and the like are inevitably generated through removal of the interfering layer. The generated substances diffuse when the voltage for measuring is applied to the working electrode. As a result, concentration measuring of an object substance with high accuracy is performed only after the diffusion current is sufficiently lowered. Concretely, when the forward measurement bias is determined to be 0.75 volts and the reverse bias for reviving is determined to be −1 volt, the diffusion current is sufficiently lowered only after 1–2 minutes after removal of the interfering layer. The disadvantage of having to wait a long time period until actual measuring can be started, arises.

On the contrary, in the present invention, substances generated through removal of the interfering layer are moved to one of the electrodes at high speed because the higher voltage is applied to the working electrode. The substances are sufficiently close to one of the electrodes, accordingly, when the measurement voltage is applied to the working electrode, thereby the substances are rapidly consumed when the measurement voltage is applied to the working electrode. As a result, a time period between removal of the interfering layer to when it is possible to start the concentration measuring of an object substance with high accuracy is remarkably shortened.

FIGS. 4(A1) through 4(B3) are diagrams useful in understanding the operation described above. FIGS. 4(A1) to FIG. (A3) correspond to a conventional case, while FIGS. 4(B1) to FIG. 4(B3) correspond to this present invention.

As is illustrated in FIGS. 4(A1) and 4(B1), the same quantity of generated substances exist between the working electrode and the reference electrode when the interfering layer is removed. Then, in the conventional case, only a fairly small moving force toward the working electrode acts on the generated substances as is illustrated in FIG. 4(A2), thereby the time period for consuming a predetermined quantity of the generated substances is lengthened. That is, the generated substances are not so close to the working electrode as is illustrated in FIG. 4(A3) after a predetermined time period has passed, thereby a long time period is needed for most of the generated substances to reach the working electrode and be consumed. On the contrary, in this present invention, a fairly large moving force toward the working electrode acts on the generated substances as is illustrated in FIG. 4(B2), thereby the generated substances are fairly close to the working electrode when a time period equal to the above described time period has passed, as is illustrated in FIG. 4(B3). Thereafter, the same moving force as in the conventional case acts on the generated substances. A time period for consuming a predetermined quantity of the generated substances is reduced because the generated substances are already close to the working electrode. As a result, the time period between removal of the interfering layer to when it is possible to start actual measuring is remarkably shortened. A biosensor having three electrodes is illustrated in FIGS. 4(A1) to 4(B3). A biosensor having two electrodes, excluding the reference electrode, is similar to the biosensor having three electrodes.

It is also an object of the present invention to suppress the degree of damage to the membrane or membranes fixed on a surface of an electrode unit.

This present invention thus first applies to a predetermined reverse bias to a working electrode for a predetermined time period, then, applies a predetermined forward measurement bias to the working electrode for a predetermined time period, at least one of the reverse bias and the forward measurement biases being a bias voltage which gradually increases in absolute value up to a predetermined value.

It is preferred that the predetermined reverse bias is a reverse bias which is gradually increased until its absolute value reaches a predetermined value, and the forward measurement bias is a forward bias which is gradually increased until its absolute value reaches a predetermined value.

It is also preferred that the increasing of the forward measurement bias is equal to the increasing of the reverse bias.

It is further preferred that the increasing of the forward measurement bias is greater than the increasing of the reverse bias.

This present invention comprises:
 reviving voltage applying means for applying a reviving voltage to a working electrode;
 measurement voltage applying means for applying a measurement voltage to a working electrode;
 time constant means for controlling at least one of the voltages applied by the voltage applying means according to a predetermined time constant.

It is preferred that the time constant means controls the reviving voltage applied by the reviving voltage applying means and the measurement voltage applied by the measurement voltage applying means according to a predetermined time constant.

It is also preferred that the time constant means applies the same time constants to both voltages applied by both voltage applying means.

It is further preferred that the time constant means applies a longer time constant to the measurement voltage applied by the measurement voltage applying means than the time constant applied to the reviving voltage applied by the reviving voltage applying means.

In this reviving method and apparatus, when an interfering layer on the working electrode which interferes with the turning on of electricity is reduced and activity of the working electrode is revived by applying the reverse bias to the working electrode, a reverse bias with gradually increasing absolute value is applied to the working electrode (refer to FIG. 9(A)) instead of a reverse bias having a constant predetermined value as applied from the beginning of reviving. Current undershoot is remarkably suppressed, accordingly (refer to FIG. 9 (B)).

As a result, destruction of the membrane or membranes fixed to the surface of the electrode unit is remarkably suppressed, thereby to increase the level of an electrical output signal output from the electrode unit, depending on an increase in the number of times a reviving operation has occurred, is remarkably suppressed. Also, the life of the membrane or membranes is remarkably lengthened.

A current overshoot is also suppressed remarkably by applying a forward measurement bias with gradually increasing absolute value. As a result, destruction of the membrane or membranes fixed to the surface of the electrode unit is further remarkably suppressed.

More specifically, the inventors recognized that a large current flowing at the instant of applying a reverse bias for reviving caused the membrane or membranes to be destroyed. The inventors considered the cause of such a large amount of current, and found the cause is that the charging current into an electric double layer increases following sudden changing of the bias. Taking this knowledge into consideration, when the bias is gradually changed instead of suddenly changing it, a large amount of current is securely prevented from flowing, and the damage to the membrane or membranes is remarkably suppressed. In other words, the life of the membrane or membranes is remarkably lengthened.

These and other objectives, features and advantages of the present invention will be more readily understood upon consideration of the present invention, taken in conjunction with the accompanying drawings.

BRIEF DESCRIPTION OF THE DRAWINGS

FIGS. 3(A) and 3(B) are diagrams showing variations of bias voltage and current when the electrode unit is revived;

FIGS. 4(A1), 4(A2), 4(A3), 4(B1), 4(B2), and 4(B3) are diagrams showing movement of substances generated through reviving of the electrode unit;

FIGS. 7(A) and 7(B) are diagrams showing variations of the bias voltage and current when the electrode unit is revived;

FIG. 8 is an electronic circuit diagram of an electrode reviving apparatus in accordance with a fourth embodiment of the present invention;

DETAILED DESCRIPTION OF THE PREFERRED EMBODIMENTS

Figure 1:
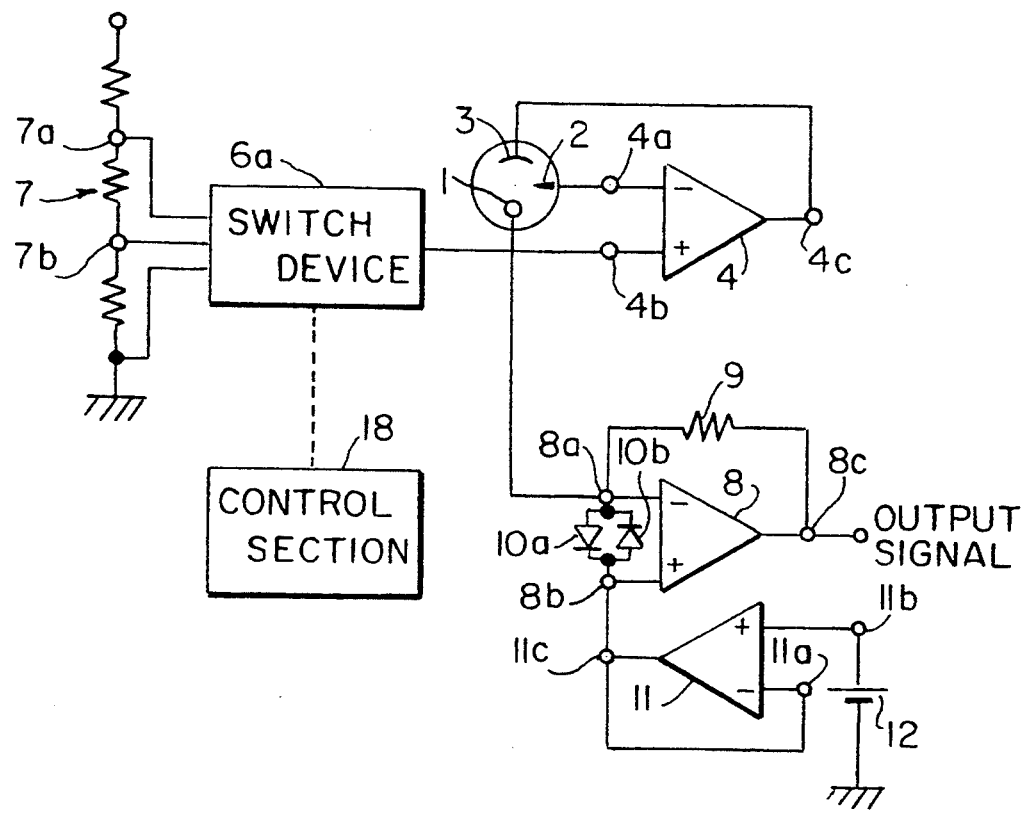
FIG. 1 is an electronic circuit diagram of an electrode reviving apparatus in accordance with a first embodiment of the present invention.

FIG. 1 is an electronic circuit diagram of an electrode reviving apparatus in accordance with a first embodiment of the present invention.

The apparatus revives an electrode unit having three electrodes, such as a working electrode 1 made of platinum, a reference electrode 2 and a counter electrode 3, both made of silver.

The reference electrode 2 and the counter electrode 3 are connected to an inverting input terminal 4a and an output terminal 4c of an operational amplifier 4, respectively. A non-inverting input terminal 4b of the operational amplifier 4 is selectively connected to a high voltage tap 7a, a low voltage tap 7b or ground of a voltage divider 7 having resistances by means of a switch device 6a. An inverting input terminal 8a of a current/voltage converting operational amplifier 8 for providing measurement signal is connected to the working electrode 1. A current/voltage converting resistance 9 is connected between an output terminal 8c and the inverting input terminal 8a of the current/voltage converting operational amplifier 8. Diodes 10a and 10b are connected in parallel and in reverse polarity with respect to one another between the inverting input terminal 8a and a non-inverting input terminal 8b of the current/voltage converting operational amplifier 8. A DC power source 12 for measuring is connected to a non-inverting input terminal 11b of a buffer amplifier 11. An output terminal 11c of the buffer amplifier 11 is connected directly to an inverting input terminal 11a of the buffer amplifier 11. The output terminal 11c of the buffer amplifier 11 is connected to the non-inverting input terminal 8b of the current/voltage converting operational amplifier 8. The DC power source 12 is used for applying a forward bias of 0.75 volts to the working electrode 1. The high voltage tap 7a and the low voltage tap 7b are used for applying biases of −1 volt and 1 volt respectively, to the working electrode 1. A control section 18, provided as a selection means, is used to control the operation of the switch device 6a.

Figure 2:
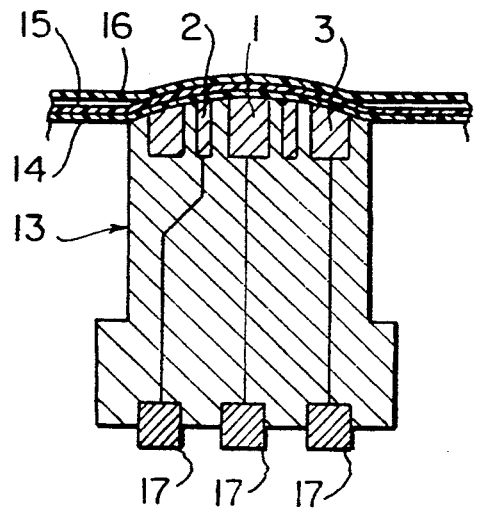
FIG. 2 is a vertical sectional view of the center portion of an electrode unit.

FIG. 2 is a vertical sectional view of the center portion of an electrode unit to which the reviving apparatus is applied.

The working electrode 1 is provided at a predetermined position in an electrode unit body 13. The ring shaped reference electrode 2 and the ring shaped counter electrode 3, both electrodes 2 and 3 surrounding the periphery of the working electrode 1, are provided in the electrode unit body 13 in this order. The electrode unit body 13 has a convex surface on the side on which the working electrode 1, the reference electrode 2 and the counter electrode 3 are provided. A hydrogen peroxide selective penetration membrane 14 made of cellulose acetate and the like, a glucose oxidaze immobilized membrane (hereinafter referred to as a GOD immobilized membrane) 15 and a diffusion-limiting membrane 16 made of polyvinyl acetate and the like are provided in this order to fit the convex surface of the electrode unit body 13. Terminals 17 for supplying output signals are provided in the electrode unit body 13. The terminals 17 are connected to the working electrode 1, the reference electrode 2 and the counter electrode 3, respectively.

The operation of the sensor for measuring glucose concentrations having the arrangement described above is as follows.

When measuring of glucose concentrations is carried out, the non-inverting input terminal 4b of the operational amplifier 4 is connected to the high voltage tap 7a of the voltage divider 7 by operating the switch device 6a. Then, a constant voltage for reviving (for example the constant voltage of −1 volt) is applied between the working electrode 1 the reference electrode 2 (Refer to a region R1 in FIGS. 3(A) and 3(B)).

In this condition, current flows to reduce interfering substances which are formed on a surface of the working electrode 1. The interfering substances are completely removed and activity of the working electrode 1 is revived by continuing to apply the constant voltage for reviving between the electrodes 1 and 2 for a fairly short time period (for example a time period of about 4 seconds). When the interfering substances are completely removed, hydrogen, hydrogen ions and the like are disposed between the working electrode 1 and the reference electrode 2.

Thereafter, the non-inverting input terminal 4b of the operational amplifier 4 is connected to the low voltage tap 7b of the voltage divider by operating the switch device 6a. Then, a higher voltage (for example the higher voltage of 1 volt) higher than a measurement voltage is applied between the working electrode 1 and the reference electrode 2 (Refer to a region R2 in FIGS. 3(A) and 3(B)).

In this condition, a large moving force acts on the floating hydrogen, hydrogen ions and the like to move them toward the working electrode 1. Most hydrogen, hydrogen ions and the like are moved close to the working electrode 1 by applying a high voltage between the working electrode 1 and the reference electrode 2 for a fairly short time period (for example, a time period of about 5 seconds).

Thereafter, the non-inverting input terminal 4b of the operational amplifier 4 is connected to ground of the voltage divider 7 by operating the switch device 6a. Then, a predetermined voltage (for example a voltage of 0.75 volts) is applied as a forward bias to the working electrode 1 on the basis of the reference electrode 2. The hydrogen, hydrogen ions and the like are consumed within a short time period, then glucose concentrations may be measured. The time period between removal of interfering substances to when measuring is permitted is 1–2 minutes in conventional reviving apparatus, while the time period is reduced to about 30–45 seconds in this embodiment.

After reviving is finished, a signal corresponding to the concentration of glucose is output as follows by dropping an object solution onto the electrode unit.

The dropped object solution is guided to the GOD immobilized membrane 15 with limited penetration by the glucose to some degree, by the diffusion-limiting membrane 16. Then, the following reaction takes place:

Hydrogen peroxide, the quantity of which corresponds to concentration of existing glucose, is accordingly generated. The generated hydrogen peroxide is guided to the surface of the working electrode 1 which is revived to have sufficient activity, through the hydrogen peroxide selective penetration membrane 14. The forward bias is kept applied to the working electrode 1. An oxidation reaction is carried out on the surface of the working electrode 1 and current corresponding to the amount of hydrogen peroxide flows in through the working electrode 1. The current is applied to the inverting input terminal 8a of the current/voltage converting operational amplifier 8, then a voltage signal is output from the output terminal 8c of the current/voltage converting operational amplifier 8. The voltage signal is generated by adding an offset voltage caused by the forward bias and a voltage signal being proportional to the current.

Thereafter, only the voltage signal proportional to the current is extracted, then the extracted voltage signal is differentiated to obtain a first-order differential value, then a peak value of the first-order differential value is detected. Finally, a glucose concentration detection signal with high accuracy is obtained by performing the necessary operations.

SECOND EMBODIMENT

Figure 5:
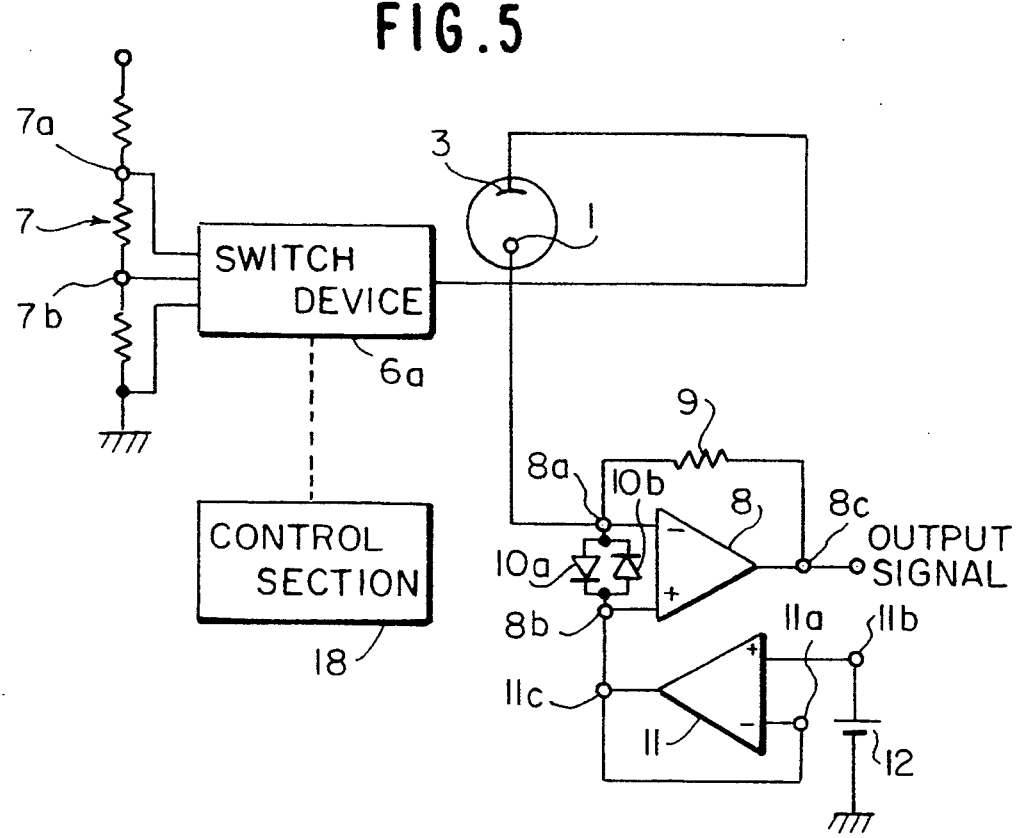
FIG. 5 is an electronic circuit diagram of an electrode reviving apparatus in accordance with a second embodiment of the present invention.

FIG. 5 is an electronic circuit diagram of an electrode reviving apparatus in accordance with a second embodiment of the present invention.

Different points from the first embodiment are as follows, (1) an electrode unit having two electrodes, one is the working electrode 1 made of platinum while another, the counter electrode 3 made of silver, is used for being revived, and (2) the counter electrode 3 is directly connected to the switch device 6a by omitting the operational amplifier 4.

In this embodiment, reviving for an electrode unit having two electrodes can be performed. Also, the time period between removal of an interfering substance to when it is possible to start actual measuring can be shortened.

THIRD EMBODIMENT

Figure 6:
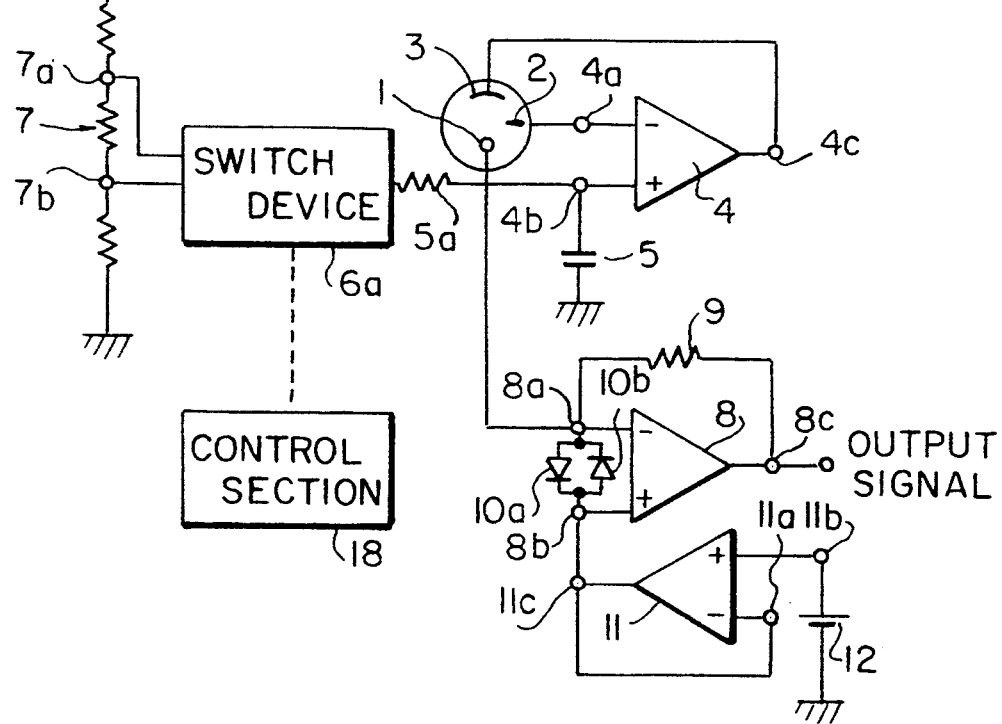
FIG. 6 is an electronic circuit diagram of an electrode reviving apparatus in accordance with a third embodiment of the present invention.

FIG. 6 is an electronic circuit diagram of an electrode reviving apparatus in accordance with a third embodiment of the present invention.

Different points from the first embodiment are as follows, (1) the non-inverting input terminal 4b of the operational amplifier 4 is connected to ground through a condenser 5, (2) the non-inverting input terminal 4b is selectively connected to the high voltage tap 7a and the low voltage tap 7b of the voltage divider 7 through a resistance 5a and the switch device 6a.

In this embodiment, bias voltages are increased in absolute value (refer to FIG. 7(A)) based on a time constant, (for example, a time constant of 0.5 seconds). The time constant is determined based on the resistance 5a and the condenser 5. As a result, current undershoots and overshoots are remarkably suppressed as is illustrated in FIG. 7(B). That is, an excessive current is securely prevented from flowing. Damage to a membrane or membranes fixed on the surface of the electrode unit, effected by the current is remarkably reduced, accordingly. As a result, the life of a membrane or membranes is extended up to about one year while the life of a membrane or membranes applied in the conventional reviving apparatus is about one month. The life is a time period when the penetration ratio of the hydrogen peroxide selective penetration membrane increases by 10%.

FOURTH EMBODIMENT

FIG. 8 is an electronic circuit diagram of an electrode reviving apparatus in accordance with a fourth embodiment of the present invention.

Different points from the third embodiment are as follows, (1) an electrode unit having two electrodes, one is the working electrode 1 made of platinum while another, the counter electrode 3 made of silver, is used for being revived, and (2) the counter electrode 3 is directly connected to the switch device 6a by omitting the operational amplifier 4.

In this embodiment, reviving for an electrode unit having two electrodes can be performed. Also, the time period between removal of interfering substances to when it is possible to start actual measuring can be shortened. Furthermore, damage to a membrane or membranes fixed on the surface of the electrode unit, effected by the current is remarkably reduced.

Figure 10:
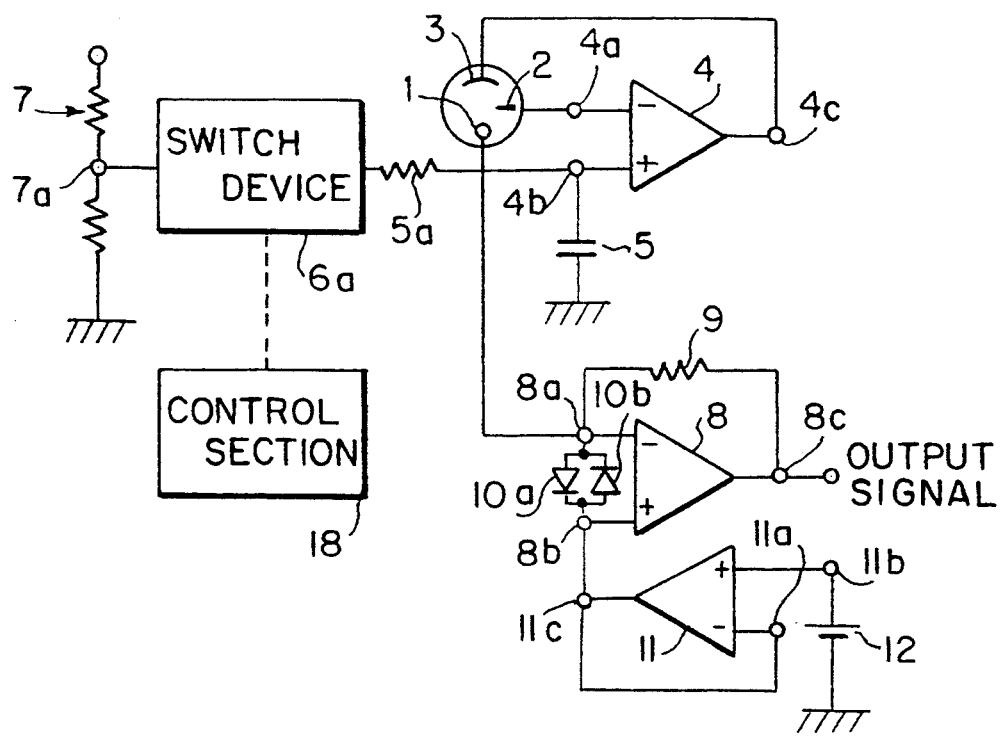
FIG. 10 is an electronic circuit diagram of an electrode reviving apparatus in accordance with a further embodiment of the present invention.

FIG. 10 is an electronic circuit diagram of an electrode reviving apparatus in accordance with another embodiment of the present invention.

The reference electrode 2 and the counter electrode 3 are connected to an inverting input terminal 4a and an output terminal 4c of an operational amplifier 4, respectively. A condenser 5, provided as a biasing voltage source, is connected between a non-inverting input terminal 4b of the operational amplifier 4 and ground. A connecting point of the condenser 5 and the operational amplifier 4 is connected to a high voltage tap 7a of a voltage divider 7 having resistances, through a resistance 5a and a switch device 6a. That is, a time constant circuit is provided by the resistance 5a and the condenser 5. An inverting input terminal 8a of a current/voltage converting operational amplifier for providing measurement signals is connected to the working electrode 1. A current/voltage converting resistance 9 is connected between an output terminal 8c and the inverting input terminal 8a of the current/voltage converting operational amplifier 8. Diodes 10a and 10b are connected in parallel and in reverse polarity with respect to one another between the inverting input terminal 8a and a non-inverting input terminal 8b of the current/voltage converting operational amplifier 8. A DC power source 12 for measuring is connected to a non-inverting input terminal 11b of a buffer amplifier 11. An output terminal 11c of the buffer amplifier 11 is connected directly to an inverting input terminal 11a of the buffer amplifier 11. The output terminal 11c of the buffer amplifier 11 is connected to the non-inverting input terminal 8b of the current/voltage converting operational amplifier 8. The DC power source 12 is used for applying a forward bias of 0.75 volts to the working electrode 1. The high voltage tap 7a is used for applying a bias of $-1$ volt to the working electrode 1. A control section 18 is used to control the operation of the switch device 6a.

Figure 9A:
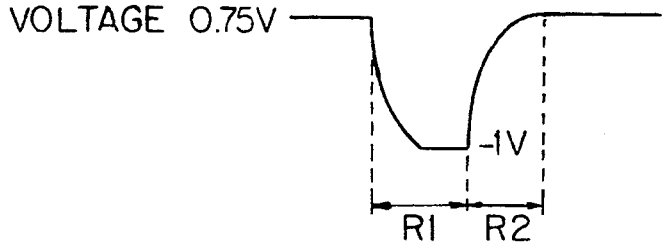
FIGS. 9(A) and 9(B) are diagrams schematically showing variations of bias voltage and current when an electrode unit is revived.
Figure 9B:
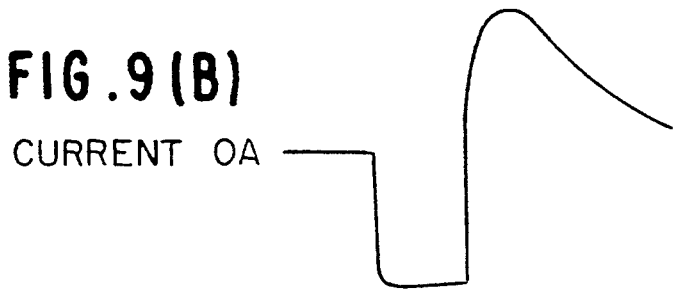

When measuring of glucose concentration is carried out, the non-inverting input terminal 4b of the operational amplifier 4 is connected to the high voltage tap 7a of the voltage divider 7 by operating the switch device 6a through the resistance 5a. When the non-inverting input terminal 4b is connected to the high voltage tap 7a through the resistance 5a, the high voltage tap 7a is to apply a reverse bias of −1 volt between the working electrode 1 and the reference electrode 2. The actual voltage applied between the working electrode 1 and the reference electrode 2 is determined based on the voltage between the terminals of the condenser 5, thereby the reverse bias gradually increases by a time constant determined by the resistance 5a and the condenser 5, as is illustrated in FIG. 9(A), region R1. The time constant has a greater value, for example 0.5 seconds, than a time constant, usually 0.001–0.1 seconds, of a CR circuit which is used for removing noise. In this condition, a current undershoot is scarcely recognized as is illustrated in FIG. 9(B), region R1. Also, the activity of the electrode unit is sufficiently revived because the current has a sufficient value to reduce interfering substances on the surface of the electrode unit.

After the reverse biasing operation is performed for a predetermined time period, the switch device 6a is operated to turn off. The DC power source 12 is to apply a forward bias of 0.75 volts between the working electrode 1 and the reference electrode 2. The actual voltage applied between the working electrode 1 and the reference electrode 2 gradually increases as is illustrated in FIG. 9(A), region R2, because the voltage between the terminals of the condenser 5 gradually decreases according to the predetermined time constant. In this condition, a current overshoot is remarkably suppressed as is illustrated in FIG. 9(B), region R2. Furthermore, the quantity of generated hydrogen, hydrogen ions and the like is lessened because a current undershoot is scarcely recognized, thereby a time period for consuming generated hydrogen, hydrogen ions and the like before it is possible to perform measuring with predetermined accuracy, is shortened. Also, accuracy of the measurement is improved because destruction of the membrane or membranes is remarkably reduced. Furthermore, the life of the membrane or membranes is extended up to about one year while the life of the membrane or membranes applied in a conventional reviving apparatus is about one month.

Figure 11:
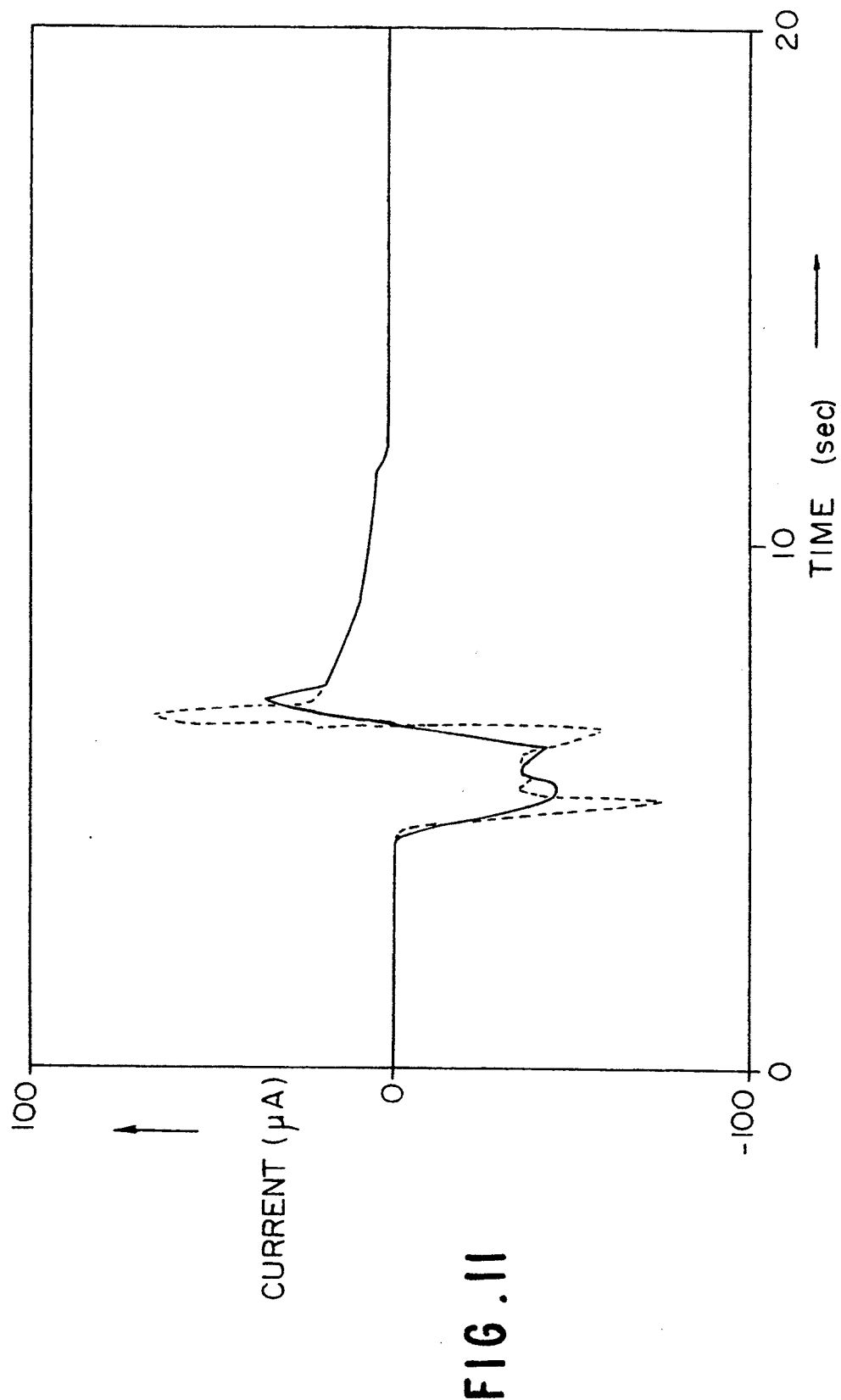
FIG. 11 is a diagram showing actual variations of current when the electrode unit is revived.

FIG. 11 is a diagram showing variations of currents, one current corresponding to the time constant of 0 seconds and another current corresponding to the time constant of 0.5 seconds. A broken line corresponds to the time constant of 0 seconds, and shows an undershoot of −78.9 micro amperes and an overshoot of 66.0 micro amperes. A solid line corresponds to the time constant of 0.5 seconds, and shows an undershoot of −48.0 micro amperes and an overshoot of 36.3 micro amperes. As is apparent from the drawing, the undershoot and overshoot are remarkably suppressed. In both cases, after the undershoot has occurred, first the current decreases in absolute value, then the current increases in absolute value. This variation of current may be caused in that the first undershoot is caused by flowing charging current, then the charging current decreases, thereafter, the surface of the electrode unit is completely charged and has a potential for generating hydrogen, thereby the current again increases in absolute value.

After reviving is finished, a signal corresponding to the concentration of glucose is output as follows by dropping an object solution onto the electrode unit.

The dropped object solution is guided to the GOD immobilized membrane 15 with limited penetration by the glucose to some degree, by the diffusion-limiting membrane 16. Then, the following reaction takes place:

$$\text{Glucose} + O_2 + H_2O \xrightarrow{\text{GOD}} \text{Gluconic acid} + H_2O_2$$

Hydrogen peroxide, the quantity of which corresponds to concentration of existing glucose, is accordingly generated. The generated hydrogen peroxide is guided to the surface of the working electrode which is revived to have sufficient activity, through the hydrogen peroxide selective penetration membrane 14. The forward bias is kept applied to the working electrode 1. An oxidation reaction is carried out on the surface of the working electrode 1 and current corresponding to the amount of hydrogen peroxide flows in through the working electrode 1. The current is applied to the inverting input terminal 8a of the current/voltage converting operational amplifier 8, then a voltage signal is output from the output terminal 8c of the current/voltage converting operational amplifier 8. The voltage signal is generated by adding an offset voltage caused by the forward bias and a voltage signal being proportional to the current.

Thereafter, only the voltage signal proportional to the current is extracted, then the extracted voltage signal is differentiated to obtain a first-order differential value, then a peak value of the first-order differential value is detected. Finally, a glucose concentration detection signal with high accuracy is obtained by performing the necessary operations.

Figure 12:
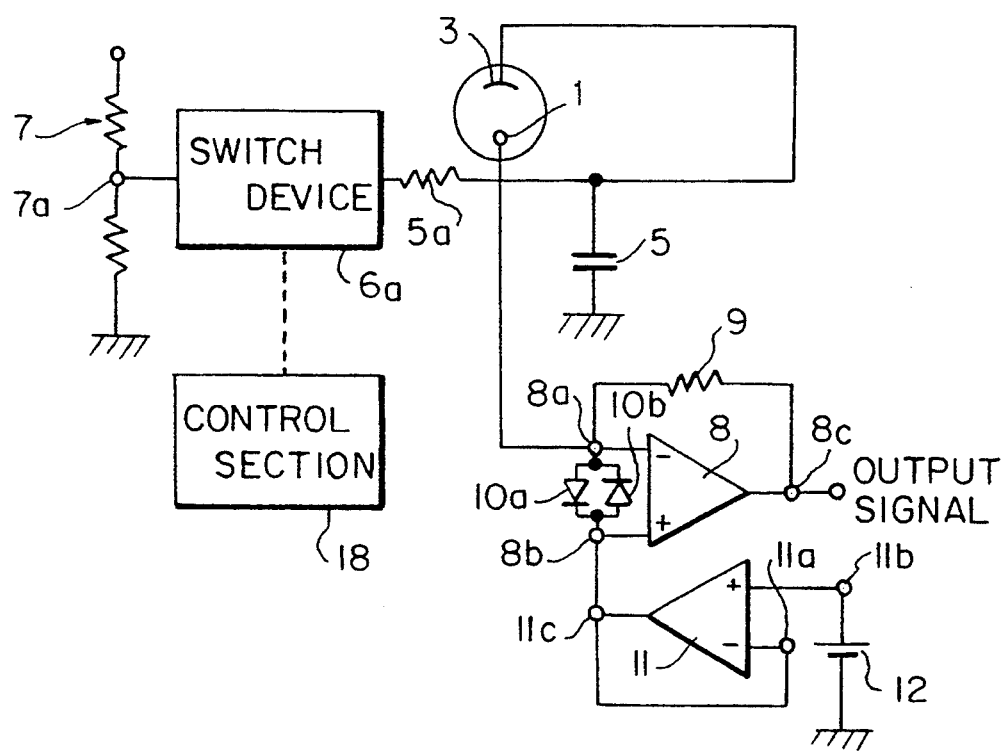
FIG. 12 is an electronic circuit diagram of an electrode reviving apparatus in accordance with still another embodiment of the present invention.
Figure 13:
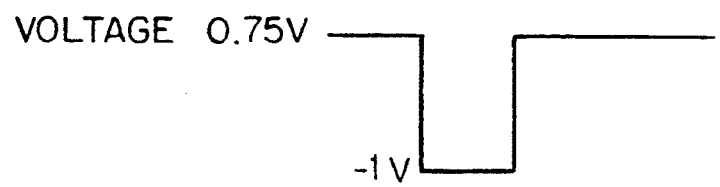
FIGS. 13(A) and 13(B) are diagrams showing variations of the bias voltage and current when the electrode unit is revived in conventional manner.
Figure 13:
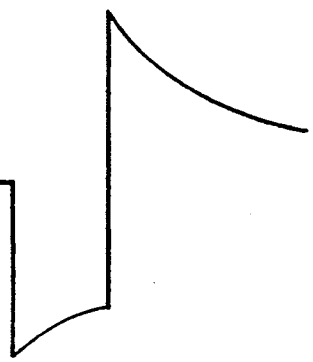

FIG. 12 is an electronic circuit diagram of an electrode reviving apparatus in accordance with still another embodiment of the present invention.

Different points form the previous embodiment are a follows:
(1) an electrode unit having two electrodes, one is the working electrode 1 made of platinum while another, the counter electrode 3 made of silver, is used for being revived, and
(2) the counter electrode 3 is directly connected to the switch device 6a by omitting the operational amplifier 4.

In this embodiment, undershoot and overshoot are remarkably reduced when the electrode unit is revived. Also, a time period between removal of interfering substances to when it is possible to start actual measuring can be shortened. Furthermore, the accuracy of measurement is improved and the life of the membrane or membranes are lengthened because the destruction of the membrane or membranes are remarkably suppressed.

This invention is not limited to the foregoing embodiments. Preferably, the voltage for reviving and higher voltage are changed. Preferably, the time period of applying voltage is changed corresponding to the voltage value. Preferably, the reviving method and apparatus are applicable to apparatus for measuring concentrations of substances other than glucose. Preferably, a programmable power source which varies the output voltage under control by a microcomputer, is employed instead of the time constant circuit comprising the resistance 5a and the condenser 5.

The terms and expressions which have been employed here are used as terms of description and not of limitations, and there is no intention, in the use of such terms and expressions of excluding equivalents of the features shown and described, or portions thereof, it being recognized that various modifications are possible within the scope of the invention as claimed.

What is claimed is:

1. A method for reviving an electrode unit of a biosensor device which includes a working electrode and a counter electrode, and which measures a concentration of an object substance based upon an electrical signal generated between the working electrode and the counter electrode when a predetermined forward measurement bias voltage is applied to the working electrode on which a physiologically active substance is placed, the electrical signal being generated based upon a biological reaction of the object substance, said method comprising the steps of:
   (1) applying a predetermined reverse bias voltage to the working electrode for a predetermined time period, and
   (2) applying a predetermined forward measurement bias voltage to the working electrode,
   wherein at least one of the bias voltages is gradually increased in absolute value according to a time constant to reach a predetermined value.

2. A method as set forth in claim 1, wherein the predetermined reverse bias voltage is gradually increased according to a first time constant until the absolute value thereof reaches a predetermined value, and the predetermined forward measurement bias voltage is gradually increased according to a second time constant until the absolute value thereof reaches a predetermined value.

3. A method as set forth in claim 2, wherein the second time constant is equal to the first time constant.

4. A method as set forth in claim 2, wherein the second time constant is longer than the first time constant.

5. A method for reviving an electrode unit of a biosensor device which includes a working electrode and a counter electrode, and which measures a concentration of an object substance based upon an electrical signal generated between the working electrode and the counter electrode when a predetermined forward measurement bias voltage is applied to the working electrode on which a physiologically active substance is placed, the electrical signal being generated based upon a biological reaction of the object substance, said method comprising the steps of:
   (1) applying a predetermined reverse bias voltage to the working electrode for a first predetermined time period, and thereafter
   (2) applying a forward bias voltage which is higher than the forward measurement bias voltage to the working electrode for a second predetermined time period before the forward measurement bias voltage is applied to the working electrode,
   wherein at least one of the reverse bias voltage, the forward bias voltage, and the forward measurement bias voltage is gradually increased in absolute value according to a time constant to reach a predetermined value.

6. A method as set forth in claim 5, wherein the predetermined reverse bias voltage is gradually increased according to a first time constant until the absolute value thereof reaches a predetermined value, and the forward bias voltage is gradually increased according to a second time constant until the absolute value thereof reaches a predetermined value which is higher than the forward measurement bias voltage.

7. A method as set forth in claim 6, wherein the second time constant is equal to the first time constant.

8. A method as set forth in claim 6, wherein the second time constant is longer than the first time constant.

* * * * *